US00PP35601P2

(12) United States Plant Patent
Meilland

(10) Patent No.: US PP35,601 P2
(45) Date of Patent: Jan. 30, 2024

(54) CLIMBING ROSE PLANT NAMED 'MEIGUNFLA'

(50) Latin Name: *Rosa hybrida*
Varietal Denomination: MEIGUNFLA

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/216,723

(22) Filed: Jun. 30, 2023

(51) Int. Cl.
*A01H 5/02* (2018.01)
*A01H 6/74* (2018.01)

(52) U.S. Cl.
USPC ..... Plt./115

(58) Field of Classification Search
USPC ..... Plt./101, 109, 115
See application file for complete search history.

(56) References Cited

U.S. PATENT DOCUMENTS

PP11,836 P2 4/2001 Radler
PP18,564 P3 3/2008 Meilland

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of climbing rose plant, referred to by its cultivar name, 'MEIGUNFLA', is disclosed. The new variety forms attractive, double, bright red colored flowers. Attractive dense, glossy foliage is formed, which contrasts beautifully with the blossoms. A climbing growth habit is displayed. The new variety is well suited for providing attractive ornamentation in the landscape.

1 Drawing Sheet

Latin name of genus and species of plant claimed: *Rosa hybrida.*

Variety denomination: 'MEIGUNFLA'.

STATEMENT REGARDING PRIOR DISCLOSURES BY THE INVENTOR

The first offer for sale of the new variety was Jul. 14, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented). The male parent (i.e., the pollen parent) of the new variety was the 'RADRAZZ' variety (U.S. Plant Pat. No. 11,836).

The parentage of the new variety can be summarized as follows:

Unnamed Seedling X 'RADRAZZ'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms bright red colored flowers,
(b) produces double flowers, and
(c) exhibits a climbing growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seedling female parent (i.e., the seed parent) exhibits a shrub growth habit, whereas the new variety exhibits a climbing growth habit. In addition, the 'RADRAZZ' variety (i.e., pollen parent) exhibits a round and bushy growth habit, whereas the new variety exhibits a climbing growth habit and the 'RADRAZZ' variety produces flowers with a lower number of petals compared to the double flower of the new variety. Moreover, the new variety can be readily distinguished from other similar non-parental varieties. For example, the 'MEIGRAPPO' variety (U.S. Plant Pat. No. 18,564) provides flowers with a lower number of petals compared to the new variety and the 'MEIGRAPPO' vareity exhibits less tolerance to diseases and particularly less tolerance to black spot (*Diplocarpon rosae*) and leaf spot (*Cercospora rosicola*) compared to plants of the new variety.

The new variety has been named 'MEIGUNFLA'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately nine years of age and were observed during April while budded on cuttings and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of nine-years-old specimens of the new variety during April while budded on cuttings and growing outdoors at Le Cannet des Maures, Var, France.

Botanical classification: *Rosa hybrida* cultivar MEIGUNFLA.

Commercial classification: Climbing Rose Plant.

Plant:

*Habit.*—Climbing.

*Height.*—Approximately 200 cm on average.

*Width.*—Approximately 300 cm on average.

Branches:

*Color.*—Young stems: commonly near Yellow-Green Group 144A more or less suffused with anthocyanin color near Greyed-Purple Group 184B. — adult wood: commonly near a color between Green Group 143B and near Yellow-Green Group 144A.

*Length.*—From the crown to the flower is typically between 100 cm to 200 cm.

*Diameter.*—Typically between 0.5 cm to 2.0 cm.

*Thorns.*—Configuration on adult stems: slightly concave, elongated and curved downwards on the upper surface and very concave on the under surface. — long prickles — quantity: approximately 7 thorns on average per 10 cm long young stem and typically between 25 to 30 thorns on average per 10 cm long adult stem. — long prickles — length: approximately 0.9 cm on average on young stems and typically between 0.5 cm to 1.0 cm on adult stems. — long prickles — width at base: typically between 1.1 cm to 1.4 cm on young stems and typically between 0.7 cm to 1.4 cm on adult stems. — long prickles — base shape: oval, elongated, long and the tip is hooked downwards on young stems and on adult stems. — long prickles — color on young stems: commonly near Yellow-Green Group 144A amply suffused with anthocyanin color near Greyed-Purple Group 184B. — long prickles — color on adult stems: commonly near Greyed-Orange Group 165B. — small prickles — quantity: approximately 7 thorns on average per 10 cm long young stem and typically more than 50 thorn per 10 cm long adult stem. — small prickles — length: typically between 0.1 cm to 0.5 cm on young stems and typically between 0.1 cm to 0.5 cm on adult stems. — small prickles — width at base: typically between 0.1 cm to 0.4 cm on young stems and typically between 0.1 cm to 0.4 cm on adult stems. — small prickles — base shape: oval, very narrow, and short on young stems and oval, narrow, and rather short on adult stems. — small prickles — color on young stems: commonly near Greyed-Purple Group 184B and near Greyed-Orange Group 164B at the top. — small prickles — color on adult stems: commonly near Greyed-Orange Group 165B.

*Internode.*—Numbers on the entire branch: typically between 20 to 50. — length: typically between 2.5 cm to 5.5 cm.

Foliage:

*General appearance.*—Dense, glossy.

*Number of leaflets.*—3, 5, 7; most often 5.

5 *leaflets leaf.*—Length: typically between 9.0 cm to 13.0 cm. — width: typically between 6.5 cm to 9.5 cm.

*Terminal leaflet.*—Length: typically between 4.5 cm to 5.5 cm. — width: typically between 2.9 cm to 3.2 cm.

*Young shoots.*—Anthocyanin coloration: commonly near Greyed-Purple Group 184B.

*New foliage.*—Upper surface color commonly near Yellow-Green Group 146A. — under surface color: commonly near Yellow-Green Group 147B more or less suffused with near Greyed-Purple Group 184B.

*Adult foliage.*—Upper surface color: commonly near Green Group 137B. — under surface color: commonly near Green Group 137C.

Leaflets:

*Shape.*—Tip piculate. — base: rounded.

*Intensity of glossiness.*—Strong.

*Texture.*—Moderately leathery.

*Smoothness.*—Upper and under surfaces are smooth.

*General appearance.*—Oval.

*Serration.*—Small and single.

*Undulation on the margin.*—Weak.

*Venation.*—Color is commonly near Yellow-Green Group 145B and pattern is imparipinnate.

*Petiole rachis.*—Color of upper surface: commonly near Yellow-Green Group 144A more or less suffused with anthocyanin color near Greyed-Purple Group 184B. — color of under surface: commonly near Yellow-Green Group 145B slightly suffused with anthocyanin color near Greyed-Purple Group 184B. — texture: upper surface is smooth, under surface is smooth. — rachis of terminal leaflet: length is typically between 2.5 cm to 3.8 cm and diameter is approximately 0.1 cm on average.

*Petioles.*—Upper surface: smooth. — under surface: smooth. — color of upper surface: commonly near Yellow-Green Group 145B. — color of under surface: commonly near Yellow-Green Group 144B slightly suffused with anthocyanin color near Greyed-Purple Group 184B. — length: typically between 2.5 cm to 3.3 cm. — diameter: approximately 0.1 cm on average.

*Stipules.*—Length: typically between 1.8 cm to 2.0 cm. — width: typically between 0.1 cm to 0.2 cm. — general appearance: narrow. — texture: smooth on upper and under surfaces. — color of upper surface: commonly near Green Group 137B. — color of under surface: commonly near Green Group 137C.

Inflorescence:

*Number of flowers per stem.*—Typically between 1 to 4 flowers per stem.

*Lastingness of the bloom.*—On the plant: typically between 10 to 12 days. — in vase: not tested.

*Bud.*—Shape: globular. — size: small. — length: approximately 2.0 cm on average. — width: approximately 2.5 cm on average. — color as calyx breaks: upper surface: commonly near Red Group 46A; basal spot is very little and color is commonly near Yellow Group 3C. under surface: commonly near Red Group 46A; basal spot is very little and color is commonly near Yellow Group 3C.

*Sepals.*—Number: commonly 5. — length: typically between 3.0 cm to 3.6 cm. — width: typically between 0.8 cm to 1.0 cm (on median part). — shape: at the top: elongate and narrow. at the base: flat at union with the receptacle. — extensions: typically 2 sepals without extensions, 3 sepals with medium extension; length of extension is typically between 0.7 cm to 1.8 cm; width of extension is typically between 0.1 cm to 0.3 cm. — upper surface: texture: tomentous. color: commonly near Green Group 143D. — under surface: texture: smooth. color: commonly near Green Group 143A.

*Receptable.*—Color commonly near Yellow-Green Group 144A sometimes suffused with near Greyed-Purple Group 184A. — length: approximately 1.1 cm on average. — width: approximately 0.9 cm on average. — surface: smooth. — shape: funnel shaped.

*Peduncle.*—Length: typically between 4.0 cm to 4.5 cm. — width: typically between 0.2 cm to 0.4 cm. — surface: very slightly prickled. — color: commonly nearYellow-Green Group 144A sometimes suffused-with near Greyed-Purple Group 184B.

*Flower.*—Diameter when open: approximately 8.0 cm on average. — depth of the flower: approximately 5.0 cm on average. — shape: cup shaped. — shape when viewed from above: irregular rounded. — shape of the upper part of the flower profile: flat. — shape of the lower part of the flower profile: flat. — type: double. — number of petals under normal conditions: approximately 100 on average. — petals: shape: obovate (rounded at the top and cuneiform at the base). texture: semi-hard. length: typically between 2.8 cm to 5.0 cm. width: typically between 2.3 cm to 4.5 cm. — undulation of the petal: absent. — reflexing of the petal: medium. — petal incision: absent. — petal arrangement: imbricated with 10 petaloids (petaloid shape is deformed petals). — petal drop: petals drop off cleanly before drying. — fragrance: none. — discoloration of the flower: no. — color when opening: basal spot on the upper surface: commonly near Yellow Group 3D. upper surface: commonly near Red Group 45A. basal spot on the under surface: commonly near Yellow Group 3D. under surface: commonly near Red Group 46A. — color of the open flower: basal spot on upper surface: commonly near Yellow Group 3D. upper surface: commonly near Red Group 45A. basal spot on under surface: commonly near Yellow Group 3D. under surface of the flower: commonly near Red Group 46A. — anthers: approximately 90 on average, length is approximately 0.2 cm on average, width is approximately 0.1 cm on average, coloration is commonly near Greyed-Orange Group 163B, and arrangement is regular around styles. — filaments: length is typically between 0.2 cm to 0.8 cm and coloration is commonly near Yellow Group 3B slightly suffused at the top with anthocyanin color near Greyed-Purple Group 184C. — styles: length is typically between 0.6 cm to 1.4 cm, coloration is commonly near Greyed-Yellow Group 161C, and number is approximately 80 on average. — stigmas: length is approximately 0.3 cm on average and coloration is commonly near Yellow Group 13A. — pollen: medium quantity; color is commonly near Yellow-Orange Group 21A. — hips: information not available.

Development:

*Vegetation.*—Strong.

*Blooming.*—Early in the season and recurrent, typically from May to October in France.

*USDA hardiness zone.*—Zone 5 to 9.

*Tolerance to disease.*—Good, and particularly against black spot (*Diplocarpon rosae*) and leaf spot (*Cercospora rosicola*).

The new 'MEIGUNFLA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIGUNFLA' characterized by the following combination of characteristics:

(a) forms bright red colored flowers, (b) produces double flowers, and (c) exhibits a climbing growth habit;

substantially as herein shown and described.

* * * * *

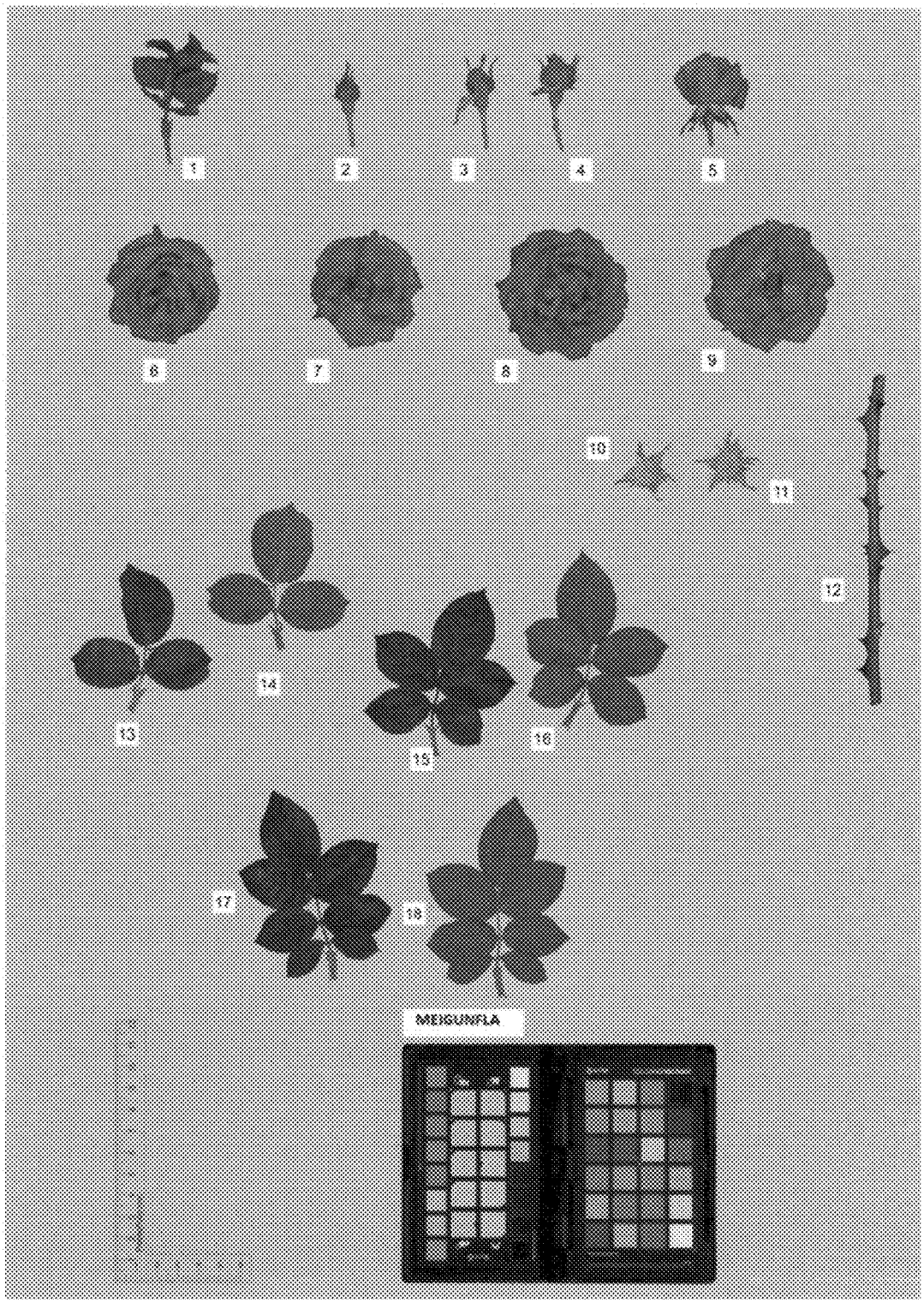
1
2
3
4
5
6
7
8
9
10
11
12
13
14
15
16
17
18
MEIGUNFLA